(12) United States Patent
Ogawa et al.

(10) Patent No.: US 7,920,266 B2
(45) Date of Patent: Apr. 5, 2011

(54) DETECTION ELEMENT, DETECTION APPARATUS FOR DETECTING TARGET SUBSTANCE, METHOD OF DETECTING TARGET SUBSTANCE AND METAL-CONTAINING MEMBER

(75) Inventors: Miki Ogawa, Machida (JP); Takeshi Imamura, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 419 days.

(21) Appl. No.: 11/941,517

(22) Filed: Nov. 16, 2007

(65) Prior Publication Data

US 2008/0117423 A1  May 22, 2008

(30) Foreign Application Priority Data

Nov. 22, 2006 (JP) ................... 2006-315715

(51) Int. Cl.
*G01N 21/00* (2006.01)
(52) U.S. Cl. ........................................ 356/445
(58) Field of Classification Search ........... 356/445–448
See application file for complete search history.

(56) References Cited

U.S. PATENT DOCUMENTS

| | | | | |
|---|---|---|---|---|
| 6,870,627 B2 * | 3/2005 | Elkind et al. | ................. | 356/445 |
| 7,456,972 B2 * | 11/2008 | Ke et al. | ................. | 356/445 |
| 2003/0132392 A1 | 7/2003 | Kuroda et al. | | |
| 2006/0160248 A1 | 7/2006 | Kamiya et al. | | |
| 2007/0264154 A1 | 11/2007 | Ojima et al. | | |
| 2009/0009756 A1 * | 1/2009 | Yamamichi et al. | .......... | 356/246 |

FOREIGN PATENT DOCUMENTS

| | | | |
|---|---|---|---|
| EP | 0 965 835 A | * | 12/1999 |
| JP | 3664401 B2 | | 4/2005 |
| JP | 2000-035685 A | | 3/2008 |
| JP | 2000-356587 A | | 3/2008 |
| WO | 2006/098502 A1 | | 9/2006 |
| WO | 2007/015556 A1 | | 2/2007 |

OTHER PUBLICATIONS

S. Link et al., "Simulation of the Optical Absorption Spectra of Gold Nanorods as a Function of Their Aspect Ratio and the Effect of the Medium Dielectric Constant," 103 J. Phys. Chem. B, 3073-77 (1999).
Shoko Kamiya et al., "Molecule Structure of Glucopyranosylamide Lipid and Nanotube Morphology," 21 Langmuir 743-50 (2005).

* cited by examiner

*Primary Examiner* — Michael P Stafira
(74) *Attorney, Agent, or Firm* — Fitzpatrick, Cella, Harper & Scinto

(57) ABSTRACT

There is provided a detection apparatus detecting target substance in a sample by utilizing plasmon resonance including a substrate and a plurality of metal-containing members arranged on the substrate, wherein the metal-containing members are shaped tubular and the metal-containing members are arranged on the substrate with a given orientation. By use hereof, a detection apparatus and a detection method enabling highly sensitive detection on target substance are provided.

4 Claims, 11 Drawing Sheets

72  71

73

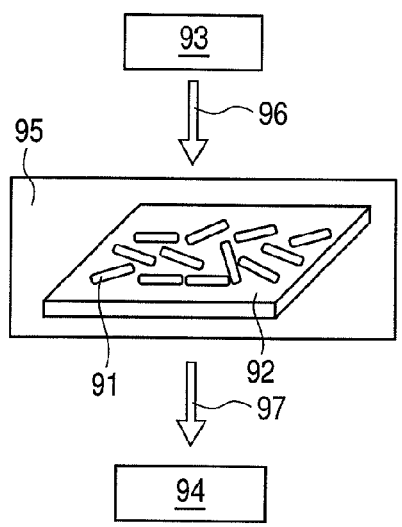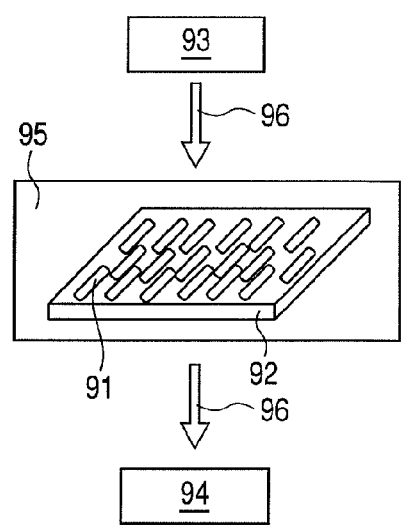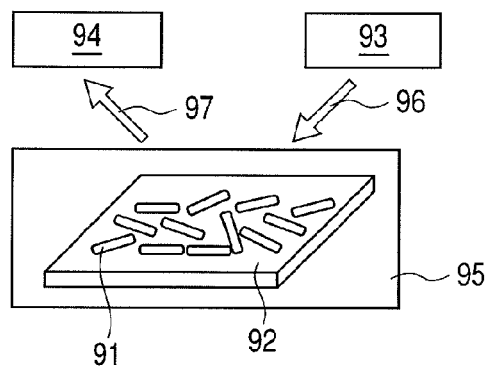

DETECTION ELEMENT, DETECTION APPARATUS FOR DETECTING TARGET SUBSTANCE, METHOD OF DETECTING TARGET SUBSTANCE AND METAL-CONTAINING MEMBER

BACKGROUND OF THE INVENTION

1. Field of the Invention

The present invention relates to a detection element, which is used for a detection apparatus for detecting a target substance in a sample by utilizing plasmon resonance, to the detection apparatus for detecting a target substance and to a metal-containing member.

2. Description of the Related Art

Biosensors are measurement devices which utilize an excellent molecular recognizing ability of living organisms or biomolecules. Combinations of biological substances which have affinity each other include, for example, enzyme-substrate, antigen-antibody, DNA-DNA etc.

Biosensors utilize the principle that one substance of the combination, which is immobilized or carried on a substrate, can selectively measure the other substance.

In recent years, biosensors are expected to have wide application not only in medical fields but also in environment, foods etc.

In order to increase the applicable area thereof, there is a need for small, light and highly sensitive biosensors which can be placed in any location or is portable.

Currently, as one of the highly sensitive sensing methods, plasmon sensors which utilize an interaction between plasmons existing on metal surface or metal microparticles and light have been vigorously studied.

Sensors using conventional surface plasmon resonance (SPR (Surface e Plasmon Resonance) sensors) utilize a phenomenon that the incident light from a specific angle resonates with metal surface plasmons and is absorbed when metal thin layer surface is irradiated with light.

The angle at which this absorbance occurs is sensitive to the surface condition of the metal thin layer (refraction index), and a reaction which occurs on a metal surface (e.g. antigen-antibody reaction) etc can be measured by measuring an intensity of reflected light while changing an angle of incidence.

However, these SPR sensors require a prism from structural reason, hence are complex in optics system.

Therefore, it is considered that there is a limitation for miniaturization.

Japanese Patent Application Laid-Open No. 2000-035685 proposes a sensor which utilizes localized plasmon resonance by metal microparticles.

The sensor disclosed in Japanese Patent Application Laid-Open No. 2000-356587 is a localized surface plasmon resonance (LSPR) sensor which detects a refraction index of a medium in the vicinity of metal microparticles by measuring an absorbance of light which transmitted through the metal microparticles immobilized like a layer on a substrate surface.

It is considered that this sensor unit does not require a prism, can be placed at narrow spaces and can be applied on a substrate having a curved surface In J. Phys. Chem. B. vol. 103, p. 3073 (1999), nanorods are prepared by using gold.

It discloses spectra based on localized plasmon resonance for these nanorods, and the relationship between an aspect ratio and a spectrum of nanorods is discussed therein.

In Japanese Patent Application Laid-Open No. 2000-356587, gold microparticles are immobilized on a surface-treated substrate by soaking the substrate in a solution of gold colloides having a diameter of about 20 nm.

The shape of gold microparticles may be close to the spherical shape. The fact is that enough sensitivity is not necessarily obtained with a plasmon sensor merely using these gold microparticles.

J. Phys. Chem. B. vol. 103, p. 3073 (1999) also discloses that the maximum absorbance wavelength is changed by making gold into a rod shape (columnar shape) and varying an aspect ratio of gold rods. However, J. Phys. Chem. B. vol. 103, p. 3073 (1999) does not disclose about orientation of gold rods and further improvement in the sensitivity is desired.

In addition, in the case of using those metal microparticles as target substance detecting material, a surface area thereof affects the sensitivity. Accordingly, if that surface area can be enlarged further, there is a possibility that the sensor can be improved further in sensitivity.

SUMMARY OF THE INVENTION

A present invention is directed to a detection element for detecting a target substance in a sample by using plasmon resonance, comprising a substrate and a plurality of metal-containing members arranged on the substrate, wherein the metal-containing members are shaped tubular and the metal-containing members are arranged on the substrate with a given orientation.

In the detection element, long axis directions of the tubular metal-containing members can be arranged parallel to the surface of the substrate.

In the detection element, long axis directions of the tubular metal-containing members can be arranged perpendicular to the surface of the substrate.

In the detection element, length a in the short axis direction and length b in the long axis direction of the tubular metal-containing member can establish b/a to fall within the range of not less than 2 and not more than 10.

A present invention is directed to a detection apparatus detecting target substance in a sample by utilizing by utilizing plasmon resonance, comprising: a detection element obtaining information on target substance in a sample by being contact with the sample; a light source for irradiating light to the detection element; and a light receiving element for receiving light emitted from the light source and reflected from or transmitted through the detection element, wherein the detection element is the above detection element.

A present invention is directed to a method of detecting target substance in a sample by utilizing by utilizing plasmon resonance, comprising: contacting the detection element according to claim 1 with a sample; irradiating light to the detection element; and receiving light reflected from or transmitted through the detection element.

In the method of detecting target substance, the light-irradiating step is a step of irradiating a polarized light. The polarized light can be biased with an direction of oscillation of an electric filed component being parallel to long axis directions of the tubular metal-containing members.

A present invention is directed to a metal-containing member used for detecting target substance in a sample by utilizing plasmon resonance, wherein the metal-containing member is tubular.

The metal-containing member can include metal film being formed on a surface of a tubular member comprised of using glycolipid.

Further features of the present invention will become apparent from the following description of exemplary embodiments with reference to the attached drawings.

BRIEF DESCRIPTION OF THE DRAWINGS

FIGS. 9A, 9B and 9C are schematic diagrams exemplifying a detection apparatus.

DESCRIPTION OF THE EMBODIMENTS (Exemplary Embodiments for Carrying Out the Invention)

A detection element of the present invention is a detection element used for detecting target substance in a sample by utilizing plasmon resonance, including a substrate and a plurality of metal-containing members arranged on the substrate surface, wherein the metal-containing members are tubular and the metal-containing members are arranged on the substrate in a given orientation. Exemplary embodiments of the present invention will be described in detail below.

(Tubular Metal-containing Member)

Figure 1:
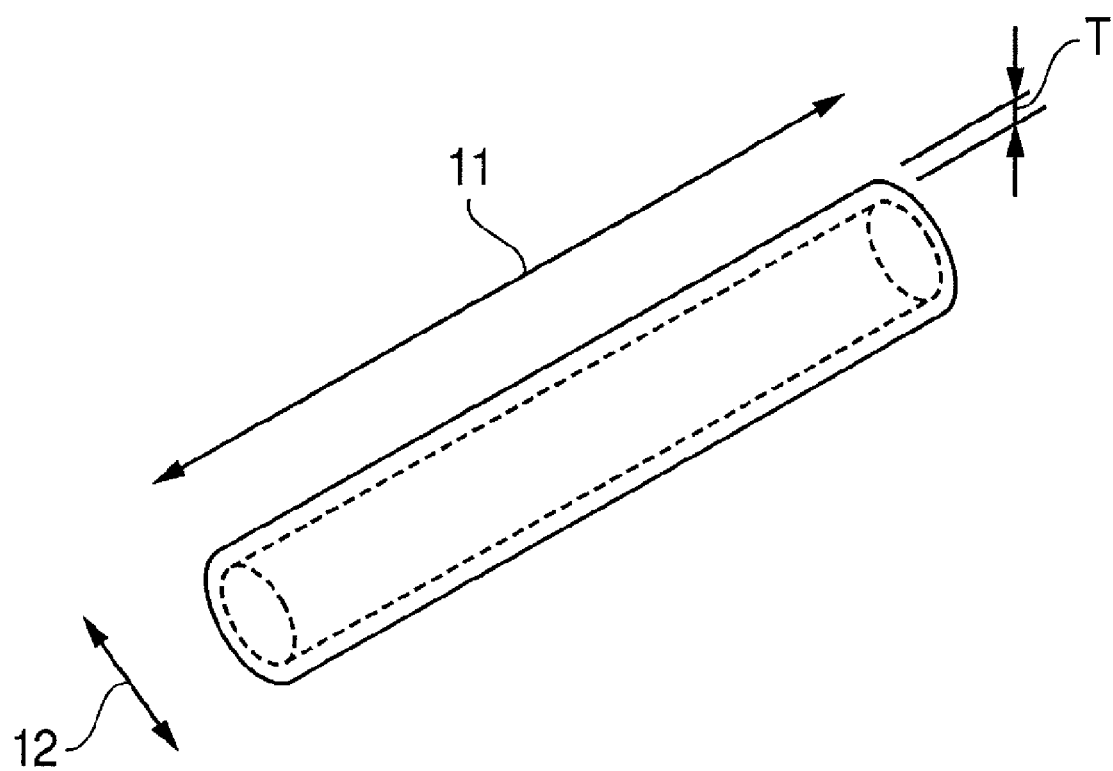
FIG. 1 is a schematic diagram illustrating a shape of a tubular metal-containing member in the present invention.
Figure 2:
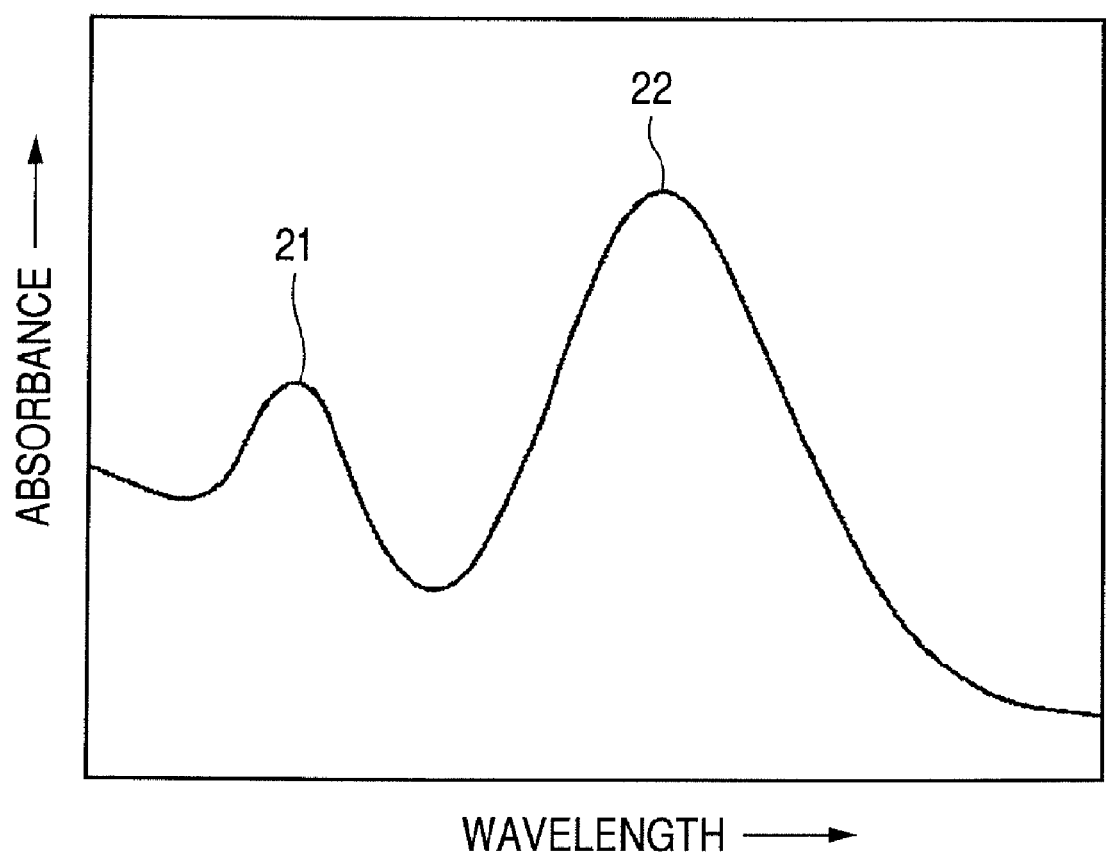
FIG. 2 is a schematic diagram exemplifying an absorption spectrum of a metal-containing member including a short axis direction and a long axis direction.

A metal-containing member in the present invention is tubular (tube-like) shape as in FIG. 1. Unlike spherical metal-containing particles, for a tubular metal-containing member configured with metal-containing particles, plasmon resonance frequencies of the short axis direction and the long axis direction are different and an absorption spectrum as in FIG. 2 is obtained. Absorption on the short wave length side in that spectrum is due to plasmon resonance in the short axis directions of tubular metal-containing members. Absorption on the long wave length side is due to plasmon resonance in the long axis directions of the tubular metal-containing members. Absorption peak on that long wavelength side is apt to be influenced by a refractive index change in the vicinity of the metal-containing members and a shift amount at the time of refractive index change is large. The present invention utilizes those phenomena. The metal-containing members are irradiated with light and property of light having been reflected from or transmitted through the metal-containing members is detected. Thereby the property (refractive index) change in the vicinity of the metal-containing members is made detectable with high sensitivity. That is, in the present invention, metal-containing members including short axis direction and long axis direction are used. By utilizing resonance in the above described long axis direction effectively, sufficient sensitivity become obtainable. In addition, since the metal-containing member according to the present invention is tubular, both surface of the outer surface and the inner surface are utilizable and the surface area can be taken largely. Therefore, an increase in carrying amount of capturing body to be described later can contribute to further enhance sensitivity.

The metal-containing members can include metal capable of giving rise to plasmon resonance phenomena. As such metal, gold, silver and copper are preferable. In particular, silver is weak in corrosion resistance and, nevertheless, high in sensitivity and preferably used. Gold can provide a detecting element having high corrosion resistance and stability and has such advantage that it is easily modified in its surface with thiol etc.; thus gold is suitably used.

Here, metal-containing members can be prepared by mixing a solution containing metal source such as gold chloride hydrate etc. with an additive such as a surfactant etc. or a pH-adjusting agent etc., and reducing the same. Such a preparation method can be applied to the present invention. However, a manufacturing method with a template to be described below in the manufacturing method is advantageous in that tubular metal-containing particles with high structural uniformity can be produced and an arrangement on a substrate is enabled with alignment with selective orientation by utilizing a template.

As for the shape of the tubular metal-containing member, the center part of the cylinder is generally hollow but will not be limited thereto. An elliptical column, a polygonal column and the like being hollow in the center part can be nominated.

The size of the tubular metal-containing member can be generally caused to fall within a range between not less than 10 nm and not more than 300 nm in one of diameter in the short axis direction and length of a side and preferably set to not less than 20 nm and not more than 200 nm. Here, thickness T of the tubular metal-containing member can be generally caused to fall within the range of not less than 2 nm and not more than 100 nm. In addition, length in the long axis direction can generally fall within the range of not less than 20 nm and not more than 3000 nm and preferably fall within the range of not less than 40 nm and not more than 2000 nm. And, in consideration of the absorption peak of plasmon resonance wavelength and the shift amount, length a in the short axis direction and length b in the long axis direction establish b/a to preferably fall within the range of not less than 2 and not more than 10.

(Capturing Body)

The metal-containing members according to the present invention preferably include, on the surface of the metal-containing member, a capturing body capturing target substance in a sample.

The capturing body for use is substance related to selection of target substance in a sample and is, for example, substance (so-called receptor) directly and selectively reactive to target substance in a sample and substance related to reaction of target substance (for example, substance selectively gives rise to catalysis to reaction of target substance).

The capturing body may also have simultaneously a function involved in indicating the presence or absence and degree of detection, for instance, the function of reacting with the substance emitted from the receptor or with a remaining substance, and being colored. The capturing body used in the present invention is selected from the group consisting of enzymes, sugar chains, catalysts, antigens, antibodies, genes, color reagent and the like but will not be limited thereto.

Next, fixation onto metal-containing particle surfaces of those capturing bodies will be described.

The above described capturing body is fixed on or carried by the metal-containing particle surfaces by covalent binding, ion binding and absorption, for example, but will not be limited thereto if those components are fixed or carried well.

In a system according to coupling, a capturing body with a reaction group capable of acting directly can be brought into direct reaction to the metal-containing particle surfaces and Cross-linked material capable of acting directly may be brought into reaction to the metal-containing particle surfaces and, moreover, the capturing body is brought into reaction to the above described cross-linked material to, thereby implement coupling. For example, in the case where the metal-containing particles contain one of gold, silver and copper, the capturing body including a thiol group and amino group can be directly brought into fixation. In addition, the metal-containing members is brought into reaction to cross-linked material such as a silane coupling agent including a thiol group, an amino group and the like and, moreover, the capturing body is coupled with that cross-linked material to, thereby, establish fixation.

In the system according to absorption, appropriately affinitive combination can be selected as combination of a capturing body with metal microparticle. In addition, the metal-containing particle surfaces once undergoes surfaces modification to form an appropriately affinitive surfaces and also enables fixation of the capturing body.

(Arrangement with Preferred Orientation)

As described above, if resonance in the long axis direction of the tubular metal-containing members is effectively utilized, sensitivity for a detection element can be improved. Accordingly, in the present invention, the tubular metal-containing members are arranged with a preferred orientation on a substrate. The arrangement with that preferred orientation means that the long axis directions of metal-containing particles are arranged in orientation parallel to the component included in light irradiated by a light source to be described later.

Figure 3A:
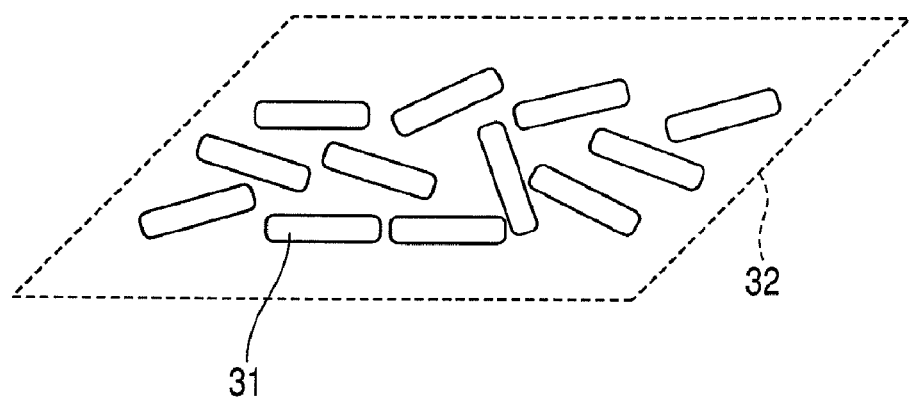
FIGS. 3A and 3B are schematic diagrams exemplifying arrangements with preferred orientation.
Figure 3B:
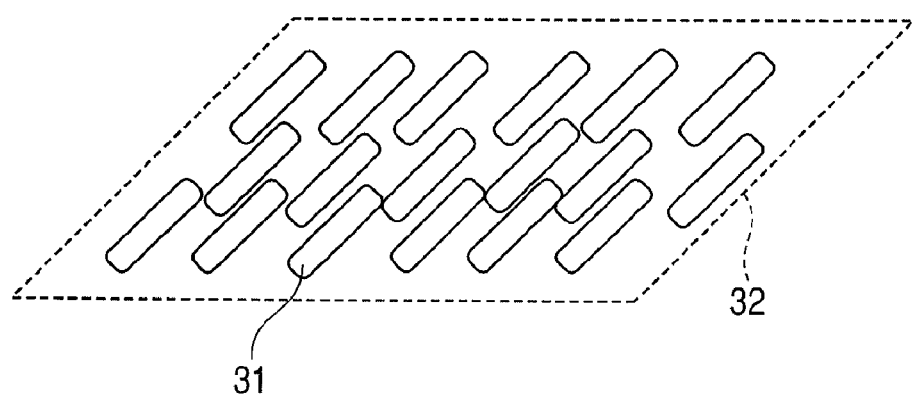

Assuming a virtual surface, an arrangement with the above described preferred orientation will be described with the drawings. Firstly, the arrangement with the preferred orientation preferably includes the long axis direction of the metal-containing members being parallel to the virtual surface 32 as in FIG. 3A. That is, uniaxially orientation is not necessarily adopted. If measurement light (incident light) incident to those metal-containing members includes components parallel to the long axis direction of the above described metal-containing members, resonance of the metal-containing members in the long axis direction can be utilized effectively. In addition, FIG. 3B schematically illustrates the arrangement with the long axis direction of the metal-containing members being directed in the uniaxially orientation. Here, in FIGS. 3A and 3B, the metal-containing members 31 are schematically illustrated as members including a tubular shape. The other drawings will be depicted likewise. Aligning a polarization direction of incident light to the long axis direction of metal-containing members enables further efficient utilization of resonance in the long axis direction.

(Detection Element)

Next, a detection element with tubular metal-containing members carried on a substrate with arrangements with the preferred orientation will be described.

Figure 4A:
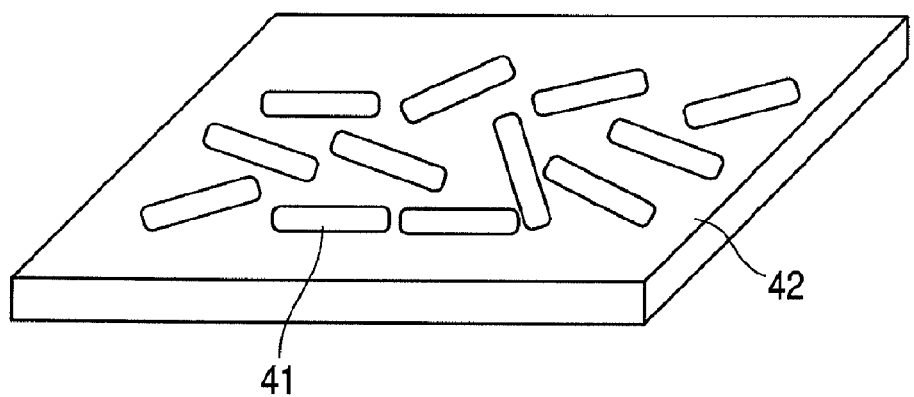
FIGS. 4A and 4B are schematic diagrams exemplifying a substrate and metal-containing members being orientated substantially in parallel in the longitudinal direction and metal-containing members being carried on the substrate.
Figure 4B:
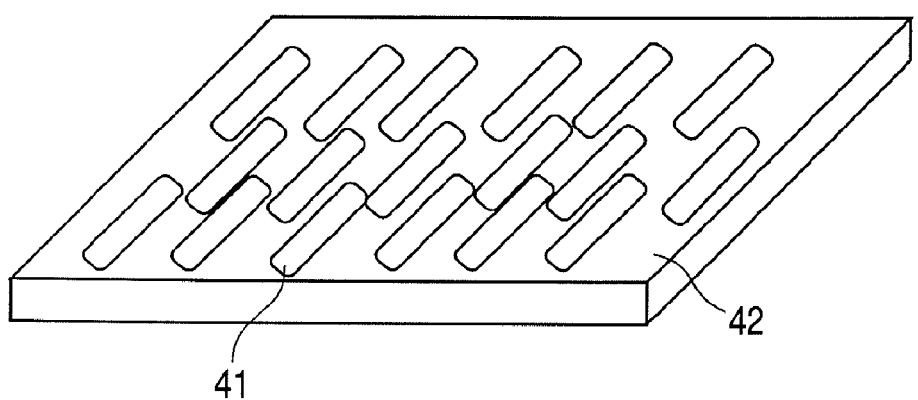

FIGS. 4A and 4B, FIGS. 5A, 5B and 5C are sectional schematic diagrams exemplifying metal-containing members with arrangements with the preferred orientation being carried on a substrate. FIGS. 4A and 4B exemplify the preferred orientation with the long axis directions of the substrate 42 and the metal-containing members 41 being arranged substantially parallel. The arrangements in FIG. 4A can be formed comparatively easily by adding the produced metal-containing members on the substrate. In contrast against FIG. 4A, FIG. 4B exemplifies the long axis directions of the metal-containing members being uniaxially orientated. That arrangement can be formed with a method of providing the substrate with grooves fixating the metal-containing members.

Figure 5A:
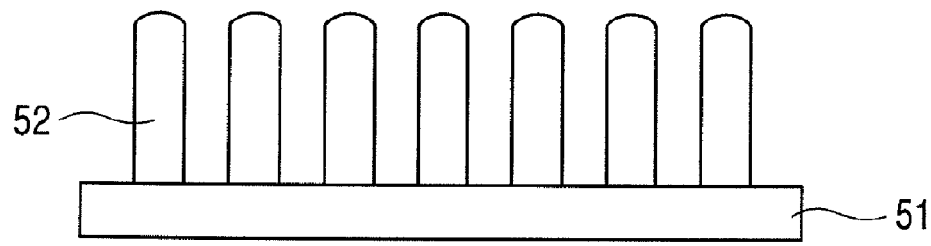
FIGS. 5A, 5B and 5C are sectional schematic diagram exemplifying metal-containing particles being carried on a substrate with preferred orientation.
Figure 5B:
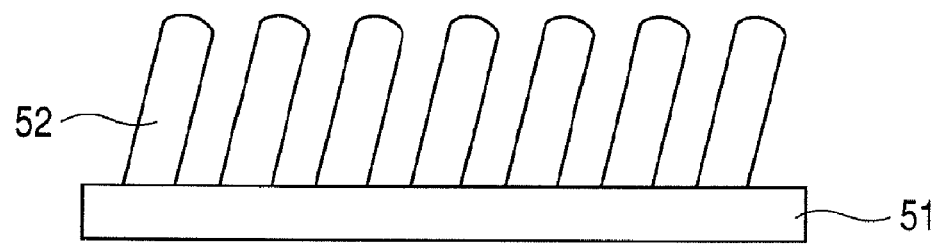
Figure 5C:
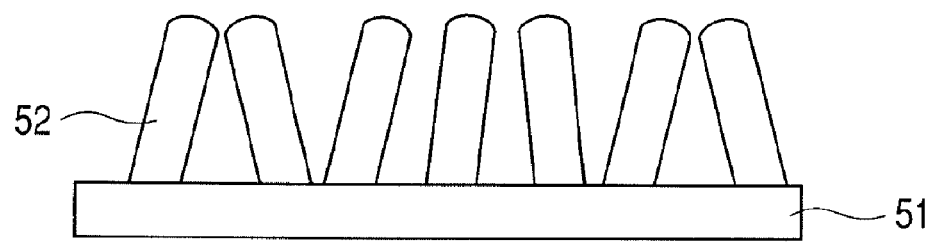
Figure 6A:
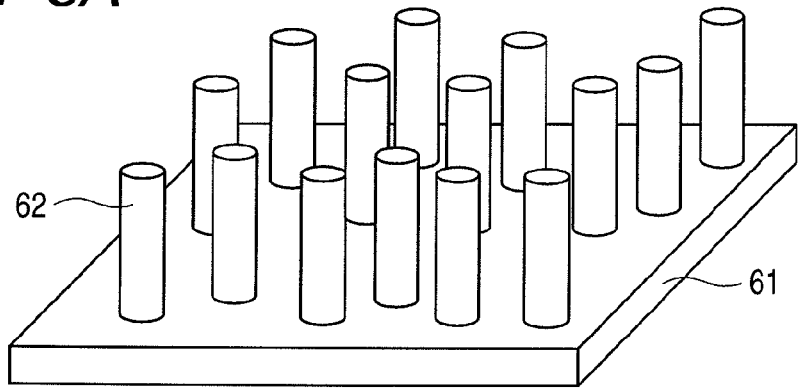
FIGS. 6A, 6B and 6C are perspective views representing metal-containing members being carried on a substrate with preferred orientation.
Figure 6B:
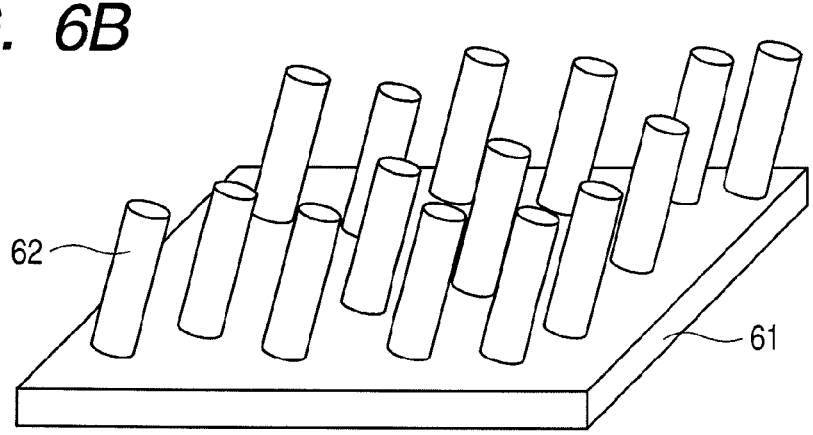
Figure 6C:
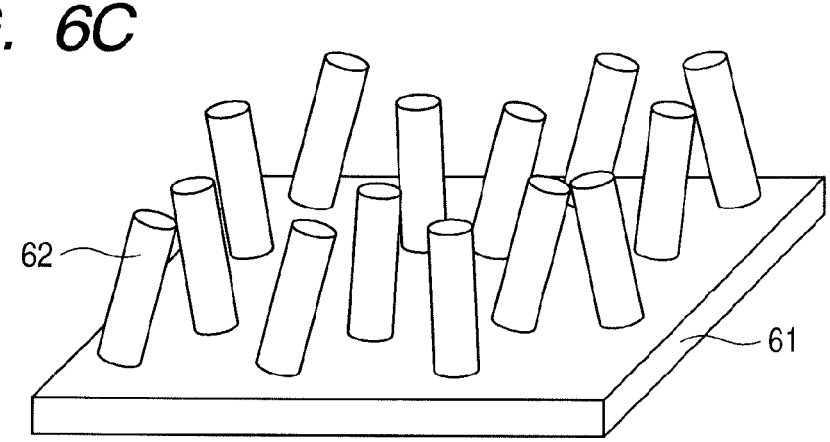

FIG. 5A exemplifies the preferred orientation substantially perpendicular to the substrate 51. Those arrangements, which will be described in the manufacturing method to be described later, can be formed by bringing porous material which become a template into contact onto the substrate to produce the metal-containing members 52 and are preferable. However, even the arrangements as in 5B, the long axis directions of the metal-containing members 52 are in parallel and are arranged with the preferred orientation. Therefore, the present invention can give rise to an effect. In addition, even with the arrangements as in FIG. 5C, the long axis directions of the metal-containing members 52 are parallel to the surface and can give rise to an effect. Here, FIGS. 5A, 5B and 5C are sectional schematic diagrams. Accordingly, on the assumption of a plurality of parallel virtual surfaces, the arrangements can be a collection of metal-containing members with the long axis directions being substantially parallel thereto. That means that the metal-containing members 62 may be arranged three dimensionally on the substrate 61 as illustrated in FIGS. 6A, 6B and 6C.

Here, if the substrate can preferably carry the metal-containing members, the substrate will not be limited due to the shape, material and the like but a general substrate made of metal, metal oxide and inorganic material such as resin, glass and silicon can be used. However, in the case of using light transmitted through the metal-containing members and further transmitted through the substrate as transmitted light for detection, the substrate is preferably made of material being transparent for the incident light and wavelength of light to be detected. In addition, light reflected by the substrate after transmitted through the metal-containing members can be used for detection as reflected light from the detection element. In that case, the substrate is preferably made of material being reflective for the incident light and wavelength of light to be detected.

In addition, in order to carry out the metal-containing members strongly, a functional group such as an amino group and a thiol group with high affinity to metal is formed on the substrate surface.

(Detection Apparatus)

A detection apparatus of the present invention includes target substance in a sample by being brought into contact with the sample; a light source for irradiating light to the detection element, a light receiving element for receiving the light emitted from the light source and reflected from or transmitted through the detection element (a light receiving element for receiving light emitted from the light source through the detection element), wherein the detection element is a detection element stipulated in the present invention.

As described above, the detection element of the present invention includes a substrate carrying tubular metal-containing members and is formed on the substrate with the metal-containing members with arrangements with the preferred orientation in the long axis direction. Accordingly, by irradiating the detection element with light including components parallel to the long axis direction of the metal-containing members, plasmon resonance in the long axis direction of the metal-containing members can occur. Light irradiated from the light source is preferably biased only to the components parallel to the long axis direction of the metal-containing members and irradiated to the detection element. However, if light includes parallel components, even nonpolarized light can give rise to the effect of the present invention.

The light receiving element detects property of light reflected by or transmitted through the detection element. Accordingly, those kinds of lights are arranged in preferably detectable positions.

(Detection Method)

A method of detecting target substance of the present invention is a method of detecting target substance in a sample by utilizing plasmon resonance, wherein a step for bringing a detection element stipulated in the present invention and a sample into contact; and a step for irradiating the detection element with light and receiving light through the detection element are included.

The step for bringing the detection element into contact with a sample including target substance changes the property in the vicinity of the metal-containing members. In particular, in the case where the detection element includes a capturing body, specific reaction between the capturing body and the target substance takes place on the detection element surface and will change the property in the vicinity of the metal-containing members. Subjected to the step for irradiating the detection element with light and the step for receiving light obtained through the detection element, the property change in the vicinity of the metal-containing members can be detected. In the case of irradiation of light including a component parallel to the long axis direction of the metal-containing members, the present invention effectively utilizes the resonance in the long axis directions of the metal-containing members to enable highly sensitive detection.

Here, measurement subject of the detection element, detection apparatus and detection method of the present invention does not necessarily need to be target substance for direct reaction by the capturing body but can be measured indirectly. For example, measurement becomes feasible by detecting target substance present in the measurement subject specifically. Accordingly, the measurement subject will not be limited to biological matter. The size thereof will not be limited, either. However, the target substance is desirably selected from the biomaterial such as sugar, protein, amino acid, antibody, antigen and quasiantigen, vitamin, gene contained in a living organism and related substance thereof as well as artificially synthesized quasi-biomaterial.

The capturing body can be used in combination, and it is possible to compose the detection apparatus such as a combined enzyme sensor, antibody-enzyme sensor, enzyme-microbial hybrid sensor, etc.

Next, a method of manufacturing the metal-containing members and the detection element will be described.

Subjected to the following the step A to the step C, the metal-containing members can be produced. Subjected to the step D, the target substance detection element can be produced.

Figure 7A:
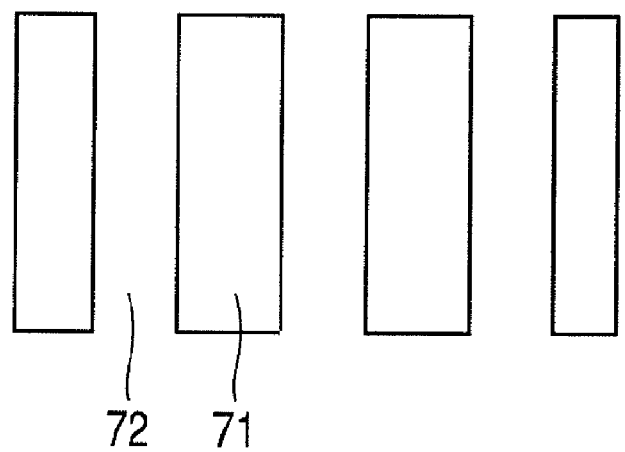
FIGS. 7A and 7B area schematic diagrams an appearance how tubular metal-containing members are formed.
Figure 7B:
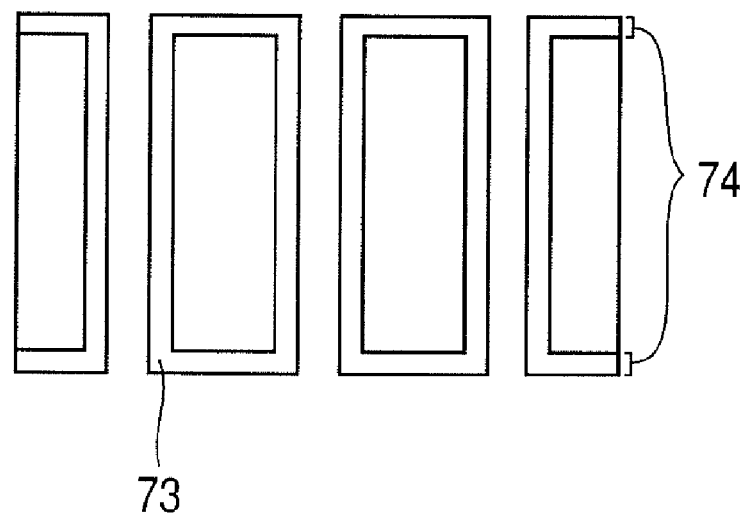

The step for preparing porous material including columnar pores (see FIGS. 7A and 7B)

In the step hereof, the porous material 71 with columnar pores 72 are prepared. The porous material will not be limited by its material, size, shape and the like if the columnar pores thereof can become a template for forming metal-containing particles. For example, the porous material provided with pores by applying processing treatment such as etching onto an arbitrary substrate and film can be used. Otherwise, anodized alumina formed by anodizing aluminum in acidic electrolyte solution includes columnar pores and can be used preferably. Here, the anodized alumina can control pore diameter and pore depth comparatively freely and, therefore, is preferable for controlling shape and size of the metal-containing particles. In addition, membrane filer made of polycarbonate and the like includes columnar pores, is being commercially available in general and can be used conveniently.

Step B Step introducing material of metal-containing members in pores of porous material In the step hereof, the porous material 71 is regarded as a template and material 73 of the metal-containing members is introduced inside the pores. Introduction to the porous material pores of the material of the metal-containing members can be carried out by evaporation, sputtering, plating and the like but will not be limited to those methods. Here, the plating method can control introduction amount of the material of the metal-containing members based on processing time and is preferably used. Shortening the processing time and, otherwise, delaying the plating velocity, the material 73 configuring the metal-containing member is formed only on the wall inside the pores as in FIGS. 7A and 7B. Subjected to the subsequent step C, the tubular metal-containing members are formed. In FIGS. 7A and 7B, 74 is a material layer of the metal-containing member formed on the porous material surface.

Step C Step of removing porous material to produce tubular metal-containing members If the porous material can be removed selectively and the tubular metal-containing members can be obtained, the method of removing the porous material will not be limited. In the present invention, the etching method is convenient, applicable to a lot of materials and, therefore, is preferably used. For example, in the case of using anodized alumina for the porous material, alumina can be removed by etching with mixed solution containing fluorinated acid, sulfuric acid, phosphoric acid, chromic acid and the like. Thus, selective removal of the porous material selectively will enable production of tubular metal-containing members as illustrated in FIG. 1. Here, in the step B, in the case of forming material layer 74 of the metal-containing members on the porous material surface as in FIGS. 7A and 7B, the following measures can be adopted in order to improve efficiency in etching the porous material and in order to improve uniformity of shape of the formed metal-containing members. That is, etching processing can be carried out after removing the layer of metal-containing members formed on the porous material by polishing and the like.

Step D Step for carrying metal-containing members on a substrate in an arrangement with preferred orientation.

Making dispersion liquid by dispersing metal-containing members produced by the steps A to C, the substrate is dipped into the dispersion liquid of the metal-containing members and otherwise the dispersion liquid of the metal-containing members is applied to the substrate. Thereby, the metal-containing members can be carried by the substrate in an arrangement of the long axis directions of the substrate and the metal-containing members as in FIG. 4A with substantially parallel preferred orientation. Here, in order to cause the substrate to carry the metal-containing members strongly, the substrate desirably undergoes surface treatment in advance to improve affinity between the metal-containing members and the substrate surface in advance. For example, in the case were the metal-containing members contains gold, a functional group selected from the group consisting of an amino group and thiol group and the like is desirably formed on the substrate surface. In addition, the substrate can be cleaned with disperse medium and the like to remove extra metal-containing members.

As in FIG. 4B, in the case where the substrate carries the metal-containing members with uniaxially-oriented arrangements of the long axis directions of the metal-containing members, a substrate with fine grooves formed on the surface can be used. By dipping and otherwise applying dispersion liquid of the metal-containing members onto a grooved substrate, the long axis directions of the metal-containing members can be arranged with the long axis directions of the metal-containing members in the almost matching directions of the grooves. Accordingly, if the grooves are formed on the substrate in a uniaxially-oriented arrangement, also the metal-containing members will be carried in a uniaxially-oriented arrangement. Here, adopting a dip coat method as the applying method, coating with the grooves and the lift up of the substrate being directed in the same direction will allow the metal-containing members to be carried by and on the substrate in more intensive uniaxially-oriented arrangement.

Figure 8:
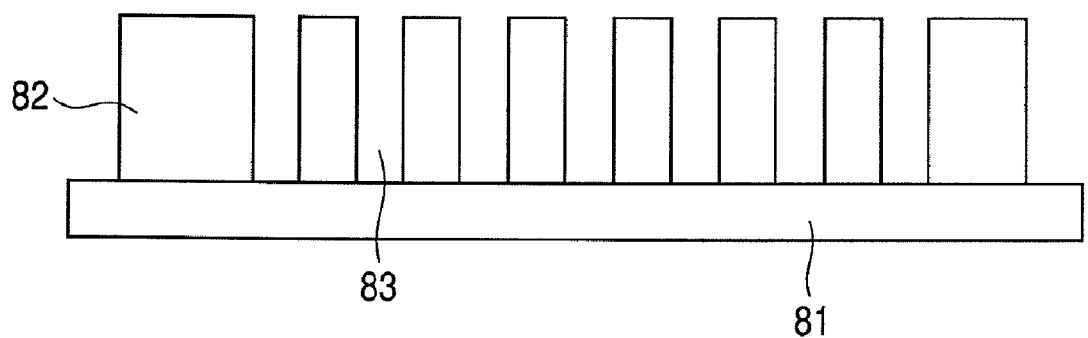
FIG. 8 is a schematic diagram exemplifying a porous material fixated on a substrate.

In the case of arranging the metal-containing members in the uniaxially-oriented arrangement as in FIGS. 5A to 5C, an operation of fixating a porous material on the substrate to produce the metal-containing members is preferably adopted as the present step. Fixing the porous material 82 prepared in the step A on the substrate 81 as in FIG. 8 and, thereafter, undergoing the step B and the step C, the metal-containing members can be arranged on the substrate in an arrangement with preferred orientation as in FIGS. 5A, 5B and 5C. Here, by changing the shape of the porous material to be used as well as the fixing position, the angle and the like of the porous material toward the substrate, the metal-containing members can be formed in desired arrangements such as arrangements with preferred orientation substantially perpendicular to the substrate as in FIG. 5A and arrangements as in FIG. 5B and FIG. 5C.

In addition, as a method of producing the tubular metal-containing members, self-organization of organic molecule can be utilized. As an example of the tubular metal-containing members obtained by that technique, metal-containing members with lipid expressed with the following Formula (1) can be nominated.

That is,

 Formula (1)

A hollow fibrous organic nanotube (tubular member) including, as a component, N-glycoside group glycolipid expressed by the formula (1) (Formula (1) includes sugar residue G except hemiacetal hydroxyl group coupled with anomeric carbon atom of sugar, and unsaturated hydrocarbon group R with carbon number of 10 to 39) is used. Those with metal film formed at least a part of the outer surface of the hollow fibrous nanotube is adopted as a metal-containing member.

Aqueous solution of N-glycoside group glycolipid expressed by the above described formula (1) is known to include nanotube being formed in a self-organization (Japanese Patent No. 03664401, Langmuir 2005, 21, p.p. 743-750). In that nanotube, amido coupling is exposed on its surface and, therefore, enable fixation of gold microparticles.

With the gold microparticles as core, gold ion solution such as chlorauric acid (HAuCl4) undergoes reduction on site. Thereby, metal film is formed on the outer surface of the hollow fibrous nanotube with N-glycoside group glycolipid expressed by the formula (1) as a component. Thus, tubular metal-containing members can be obtained.

EXAMPLES

The present invention will be described further in detail below with examples. However, the present invention will not be limited to those examples but can be modified freely in the range as far as a detection element and a detection apparatus provided with likewise function and effects according to material, composition conditions and reaction conditions and the like are obtainable.

Example 1

The present example is an example of producing tubular metal-containing members made of gold as target substance detection material and fixing a rabbit anti-mouse IgG antibody as a capturing body onto the surface of those metal-containing members.

At first, tubular metal-containing members made of gold are produced.

An aluminum substrate is prepared and cleaned with pure water and isopropyl alcohol. The aluminum substrate subjected to cleaning undergoes anodization at 40 V in solution of phosphoric acid 0.3M, the aluminum surface is oxidized to form alumina and, at the same time, columnar pores are formed so that a porous material is formed. The above described porous material is dipped into 5 wt % phospheric acid for a predetermined time. Then, the diameter of the pores can be enlarged and a porous material with a desired pore size can be obtained. In addition, changing the kind of acid used at the time of anodization, the pore-to-pore distance can be changed.

Next, gold is introduced inside the pores of that porous material with an electroless plating method. At that occasion, controlling plating velocity and plating time, a state where gold is deposited only on the wall surfaces of the pores of the porous material (FIGS. 7A and 7B). Thereafter, the porous material is dipped in 5 wt % phosphoric acid so that the porous material is selectively melted and removed to produce tubular metal-containing members. And centrifugation separates and cleans the metal-containing members.

By controlling conditions with the operations as described above, the tubular metal-containing members with diameter of 50 nm, length of 150 nm and thickness of 15 nm can be produced.

Next, an antibody is fixed on the surfaces of thus obtained metal-containing members as a capturing body. For the present embodiment, rabbit anti-mouse IgG antibody is used as the antibody.

At first, the above described tubular gold-containing members are dipped in ethanol solution of 11-Mercaptoundecanoic acid with thiol group being highly affinitive to gold. That operation exposes a carboxyl group on the surfaces of the metal-containing members. Next, a dip is likewise carried out in in 1-Ethyl-3-[3-dimethylaminopropyl]carbodiimide-hydrochloride (produced by Dojindo Laboratories) aqueous solution and N-Hydroxysulfosuccinimide (produced by Dojindo Laboratories) aqueous solution. Those operations will expose a succinimide group on the surfaces of the metal-containing members. Subsequently, the metal-containing members are dipped in rabbit anti-mouse IgG antibody/tris-hydrochloric acid buffers (pH 8.0). The above described succinimide group formed on the surfaces of the metal-containing members is reacted with an amino group of the rabbit anti-mouse IgG antibody to fix the rabbit anti-mouse IgG antibody on the gold-containing members surfaces. Here, the succinimide group not reacted yet on the gold-containing members surface can be caused to depart by adding Hydroxylamine Hydrochloride.

Subjected to the above described operations, the target substance detection material including rabbit anti-mouse IgG antibody can be produced as a capturing body on the surfaces of the tubular metal-containing members.

Example 2

The present example is an example of producing tubular metal-containing members made of gold and producing a substrate and a detection element, the detection element carrying metal-containing members on the substrate with the long axis directions of the metal-containing members being arranged substantially in parallel with preferred orientation.

At first, with a likewise method as in example 1, tubular metal-containing members are produced. Those metal-containing members are dispersed in the liquid to produce dispersion liquid of the metal-containing members. At that case, a dispersing agent is preferably used to improve dispersive power.

Next, a glass substrate with the surface having undergone amination treatment is prepared as the substrate used in the detection element. The amination treatment can be carried out easily by dipping the glass substrate in the aminosilane solution and cleaning.

The glass substrate is dipped in dispersion liquid of the metal-containing members and, thereafter, cleaned with dispersion medium.

Subjected to the above described operations, a detection element carrying tubular metal-containing members being arranged with preferred orientation as illustrated in FIG. 4A can be produced on a glass substrate.

Example 3

The present example is an example of producing tubular metal-containing members made of gold and producing a substrate and a detection element, the detection element carrying metal-containing members on the substrate with the long axis directions of the metal-containing members being arranged substantially in a uniaxial direction with preferred orientation.

As in the present example, the metal-containing members are orientated in a uniaxial direction so that the light irradiated onto the metal-containing members is biased with the direction of oscillation of the electric field component being in parallel to the long axis direction of the metal-containing members. Thereby the absorption peak of the short wave length side in FIG. 2 can be lowered. Thereby, clearer detection of the absorption peak of the long wavelength side becomes feasible.

At first, with a likewise method as in the example 1, tubular metal-containing members are produced. Those metal members are dispersed in the liquid to produce dispersion liquid of the metal-containing members. At that case, dispersing agent is preferably used to improve dispersive power.

Next, a quartz glass substrate is prepared as the substrate used in the detection element and, with photolithography technique, a plurality of linable grooves is formed on the substrate surface. Width of the groove is around 100 nm. The amino group is formed on that substrate surface with aminosilane coupling agent. Next, dispersion liquid of the metal-containing members is applied onto that quartz glass substrate with dip coat method. Here, the pull-up direction of the substrate and the directions of the grooves are preferably set to the same direction.

Subjected to the above described operations, a detection element carrying tubular metal-containing members being orientated in the long axis direction of the metal members as illustrated in FIG. 4B can be produced on a quartz glass substrate.

Example 4

The present example is an example of producing tubular metal-containing members made of gold with the detection element carrying metal-containing members on the substrate with the long axis directions of the metal-containing members being orientated substantially perpendicular to the substrate surface, and producing a detection element inside a flow channel.

The present invention is applicable to inside flow channels and, therefore, microchipping is feasible as well. In addition, since a great number of the tubular metal-containing members can be formed inside flow channels, an improvement in reaction efficiency becomes feasible.

At first, with a likewise method as in the example 1, a porous material is produced. Next, that porous material is closely-attached and fixated in the region on the glass substrate to become a flow channel later. The rest of the region to become a reactive region later is masked and gold is introduced inside the pores of the porous material on the reactive region with electroless plating method. Thereafter, subjected to a dip in 5 wt % phosphoric acid, the porous material is dissolved and removed to produce tubular metal-containing members 52 made of gold on the substrate 51 as in FIG. 5A.

Figure 11A:
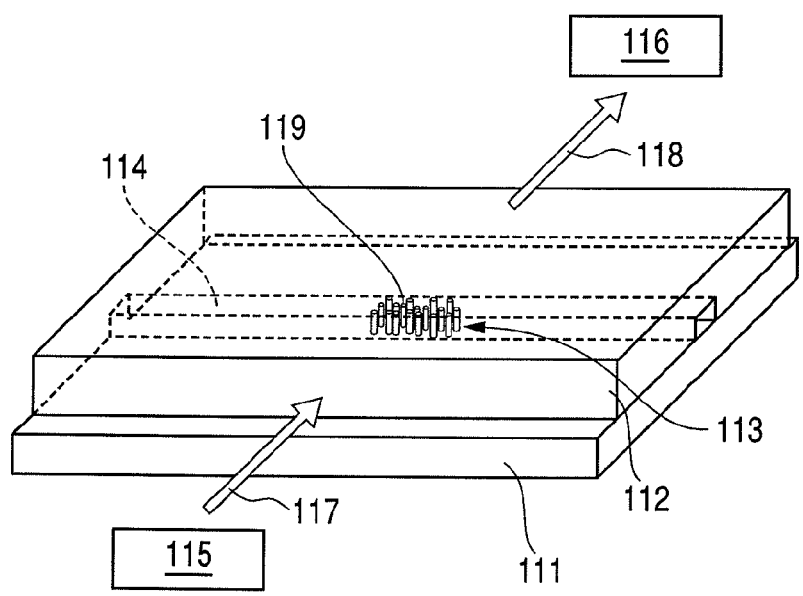
FIGS. 11A and 11B are schematic diagrams exemplifying a detection apparatus according to an embodiment.
Figure 11B:
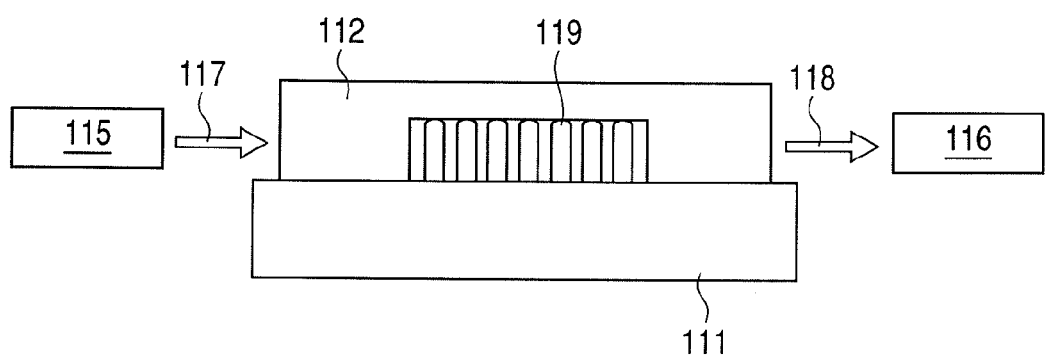

Next, a cover of resin provided with grooves is fixated on the glass substrate to produce a flow channel. At that time, the cover 112, the substrate 111 and the reactive region 113 are arranged as in FIGS. 11A and 11B so that the reactive region with the tubular metal-containing members being formed inside a flow channel is arranged and to, thereby, produce a detection element. FIGS. 11A and 11B include metal-containing members 119 and a flow channel 114. In addition, a light source 15, a light receiving element 116 and measurement lights 117 and 118 are included.

Subjected to the above described operations, a detection element carrying tubular metal-containing members with the long axis directions being orientated perpendicular to the substrate surface as illustrated in FIG. 5A can be produced.

Example 5

The present example is an example of producing a detection apparatus provided with the detection element and detecting target substance with light transmitted through the detection element.

The detection element is produced with a likewise method as in the example 2.

Next, an antibody is fixated on the surfaces of the tubular metal-containing members as a capturing body. For the present example, a rabbit anti-mouse IgG antibody is used as the antibody.

At first, ethanol solution of 11-Mercaptoundecanoicacid with a thiol group being highly affinitive to gold is applied on a glass substrate carrying metal-containing members. That operation exposes a carboxyl group on the surfaces of the metal-containing members. Next, application of 1-Ethyl-3-[3-dimethy l aminopropyl]carbodiimide hydrochloride (produced by Dojindo Laboratories) aqueous solution and N-Hydroxysulfosuccinimide (produced by Dojindo Laboratories) aqueous solution is likewise carried out. Those operations will expose a succinimide group on the surfaces of the metal-containing members. Subsequently, the glass substrate carrying the metal-containing members is dipped in rabbit anti-mouse IgG antibody/tris-hydrochloric acid buffers (pH 8.0). The above described succinimide group formed on the surfaces of the metal-containing members is reacted with an amino group of the rabbit anti-mouse IgG antibody to fix the rabbit anti-mouse IgG antibody on the metal-containing member surfaces.

Subjected to the above described operations, the detection element with a rabbit anti-mouse IgG antibody as a capturing body can be produced.

Next, an example of detection apparatus provided with the detection element will be described. Here, the present example is an example of carrying out detection with light transmitted through the detection element.

FIG. 9A is a diagram schematically illustrating the detection apparatus according to the present example. The detection apparatus includes a detection element 95, a light source 93 and the light receiving element 94. The position of the light source 93 at the time of detection is a position capable of irradiating measurement light 96 including parallel components to the long axis direction of the tubular metal-containing members 91 inside the detection element 95 as schematically illustrated in FIG. 9A. The position of the light receiving element 94 is a position capable of detecting property of the measurement light 97 transmitted through the detection element 95. Here, otherwise, a spectrodetector not illustrated in the drawing may be provided in the light receiving element 94. Moreover, an arithmetic apparatus computing the detected property change and a display unit and the like displaying the results are not illustrated in the drawing but preferably provided.

Next, an example of a detection method with that detection apparatus will be described.

At first, the detection element 95, the light source 93 and the light receiving element 94 are arranged to establish the above described positional relation and a spectrum is detected.

Thereafter a sample made of phosphoric acid buffers including mouse IgG as target substance is given to the detection element 95 and is brought into contact with the detection element 95 and reaction with a capturing body. After that reaction, the surface of the detection element 95 is preferably cleaned with the phosphoric acid buffers. Thereafter, the detection element 95, the light source 93 and the light receiving element 94 are arranged to establish a likewise positional relation as described above and a spectrum is detected.

Spectrum change before and after giving the sample is originated by change in local plasmon resonance of the tubular metal-containing members and means an occurrence of antigen-antibody reaction on the detection element and capturing of the target substance by the capturing body. Accordingly, detection of the spectrum change enables detection of the target substance in the sample.

In addition, as for the relation between the change in spectrum and target substance concentration, the relation between change in spectrum and concentration is acquired in advance with a standard sample with a plurality of known concentration. Based on that relation, calibration curve is obtained and a function between the spectrum change and concentration is obtained in advance. With that function, target substance concentration can be obtained from the spectrum change at the time of actual measurement.

Here, change in spectrum is described, but that spectrum change can be change in spectrum peak with maximum value of wavelength and can be change in peak shape such as half bandwidth of the spectrum peak. Moreover, optical intensity at one or a plurality of wavelength points may be used.

As described above, the present invention enables detection of target substance in a sample with sufficient sensitivity.

Example 6

The present example is an example of producing a detection apparatus provided with the detection element and detecting target substance with light reflected by the detection element.

The detection element is produced with a likewise method as in the example 2.

Next, an antibody is fixated on the tubular metal-containing members as a capturing body. For the present example, a rabbit anti-mouse IgG antibody is used as the antibody and fixation is carried out with a method likewise in the example 5.

Next, an example of detection apparatus provided with the detection element will be described.

FIG. 9C is a diagram schematically illustrating the detection apparatus according to the present example. The detection apparatus includes a detection element 95, a light source 93 and the light receiving element 94. The position of the light source at the time of detection is a position capable of irradiating measurement light 96 including parallel components to the long axis direction of the tubular metal-containing members inside the detection element 95 as schematically illustrated in FIG. 9C. The position of the light receiving element is a position capable of detecting property of the measurement light 98 reflected by the detection element. Here, otherwise, a spectrodetector not illustrated in the drawing may be provided in the light receiving element. Moreover, an arithmetic apparatus computing the detected property change and a display unit and the like displaying the results are not illustrated in the drawing but preferably provided.

Next, an example of a detection method with that detection apparatus will be described.

At first, the detection element, the light source and the light receiving element are arranged to establish the above described positional relation and a spectrum is detected. Thereafter a sample made of phosphoric acid buffers including mouse IgG as target substance is given onto the substrate and the sample is brought into contact with the detection element and reaction with a capturing body. After that reaction, the surface of the detection element is preferably cleaned with the phosphoric acid buffers. Thereafter, the detection element, the light source and the light receiving element are arranged to establish a likewise positional relation as described above and a spectrum is detected.

Here, target substance concentration can be obtained by obtaining calibration curve as in the example 5.

In addition, likewise in the example 5, the spectrum change can be change in spectrum peak wavelength and change in peak shape of the spectrum peak can be used. Moreover, optical intensity at one or a plurality of wavelength points may be used.

As described above, the present invention enables detection of target substance in a sample with sufficient sensitivity.

Example 7

The present example is an example of producing a detection apparatus provided with the tubular metal-containing members being orientated in the uniaxial direction and detecting target substance with light transmitted through the detection element.

As in the present example, a detection element with the tubular metal-containing members orientated in a uniaxial direction is used so that the light irradiated onto the detection element is biased with the direction of oscillation of the electric field component being in parallel to the long axis direction of the metal-containing members. Thereby the short wavelength absorption peak in FIG. 2 can be lowered. Thereby, clearer detection of the long wavelength absorption peak becomes feasible.

The detection element is produced with the likewise method as in the example 3.

Next, an antibody is fixated on the metal-containing members as a capturing body. For the present example, a rabbit anti-mouse IgG antibody is used as the antibody and fixation is carried out with a method likewise in the example 5.

Next, an example of detection apparatus provided with the detection element will be described.

FIG. 9B is a diagram schematically illustrating the detection apparatus according to the present example.

The components of the detection apparatus illustrated in FIG. 9B are likewise the components described in FIG. 9A and FIG. 9C but are different in the point that the detection element with the long axis directions of the metal-containing members 91 being parallel to the substrate surface and being orientated in the long axis direction is used and the point that the light transmitted through the detection element is measured.

The detection method is as described above.

Example 8

The present example is an example of producing a detection apparatus provided with the detection element and detecting a plurality of target substance.

According to the present example, a plurality of reactive regions carrying a capturing bodies on the substrate can be formed to enable multiple detection.

The detection element is produced with the likewise method as in the example 2.

Next, an antibody is fixated on the surfaces of the tubular metal-containing members as a capturing body. For the present example, an anti-CEA antibody, an anti-AFP antibody, an anti-PSA antibody and an anti-PAP antibody are used as the antibody.

Figure 10:
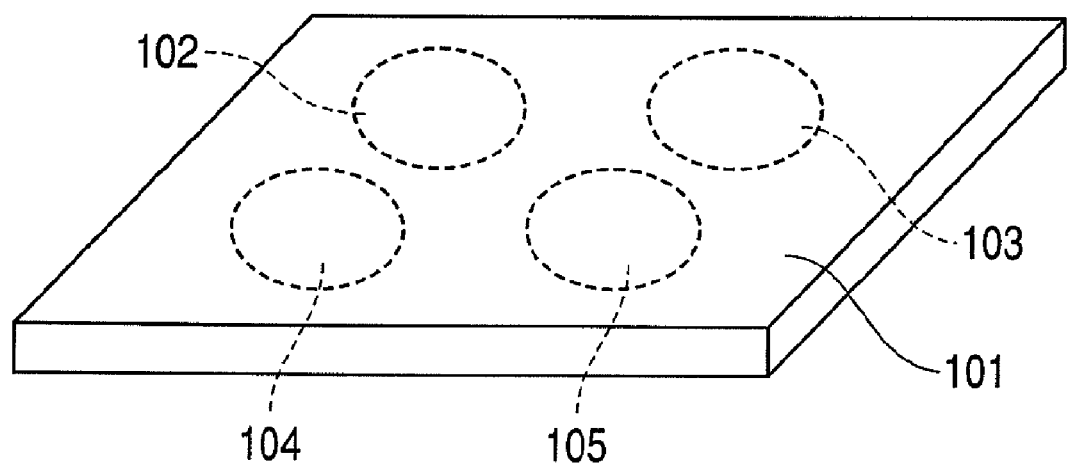
FIG. 10 is a schematic diagram exemplifying a reaction range on a substrate according to an embodiment 8.

At first, the metal-containing members undergo surface modification with ethanol solution of 11-Mercaptoundecanoic acid with a thiol group being highly affinitive to gold. At that occasion, as illustrated in FIG. 10, a stipulated amount of solution is dripped with a spotter only in the reactive region. Thereby operation exposes a carboxyl group on the surfaces of the metal-containing members. Moreover, 1-Ethyl-3-[3-dimethylaminopropyl]carbodiimidehydrochloride (produced by Dojindo Laboratories) solution and N-Hydroxysulfosuccinimide (produced by Dojindo Laboratories) solution is likewise dripped with a spotter only in the reactive region. Thereby, those operations expose a succinimide group on the surfaces of the metal-containing members. An antibody is fixed on those metal-containing members. At that occasion, as illustrated in FIG. 10, an anti-CEA antibody, an anti-AFP antibody, an anti-PSA antibody and an anti-PAP antibody are given onto the reactive regions A to D (101 to 105) on the substrate 101 respectively and are fixated.

Subjected to the above described operations, the detection element with a plurality of antibodies as a capturing body can be produced.

The detection apparatus in the present example is likewise the one illustrated in FIG. 9A used in the example 1. Here, in the present example, detection is carried out for a plurality of reactive regions. Accordingly, the light source and the detection element can be provided in the respective reactive regions. In addition, a transportation unit for arranging the respective reactive regions in the detection positions for the light source and the light receiving element and, on the contrary, a transportation unit for arranging the light source and the light receiving element in the detection positions for the respective reactive regions can be arranged. Moreover, a unit and like for refracting the measurement light in the detectable directions can be provided for the respective reactive regions.

At first, the detection element, the light source and the light receiving element are arranged and a spectrum is detected. Thereafter, likewise in the example 5, a sample made of phosphoric acid buffers including CEA as target substance is given onto substrate and is brought into contact with the detection element and reaction with a capturing body. After that reaction, the phosphoric acid buffers are preferably used for cleaning. Thereafter, the detection element, the light source and the light receiving element are arranged to establish a likewise positional relation at the above described detection and a spectrum is detected on each reactive region. Moreover, target substance respectively including AFP, PSA and PAP also undergo likewise reaction and cleaning and a spectrum is detected.

In the case of providing a plurality of reactive regions on the detection element and carrying respectively different capturing bodies as in the present example, and in the case of occurrence of respective antigen-antibody reactions, spectrum change is observed for the reactive regions corresponding thereto. Even in the case of giving a plurality of those antigens concurrently, each reactive region gives rise to a reaction to enable observation of spectrum change.

As described above, the present invention will enable detection of a plurality of target substances in a sample with sufficient sensitivity.

Example 9

The present example is an example of producing a detection apparatus provided with a detection element inside a flow channel to continuously detect target substance.

The present invention is applicable to inside flow channels and, therefore, microchipping of a detection apparatus is feasible as well. In addition, since a great number of the tubular metal-containing members can be formed inside flow channels, an improvement in reaction efficiency becomes feasible.

The detection element is produced with a likewise method as in the example 4.

Next, an antibody is fixated on the surface of the tubular metal-containing members as a capturing body. For the present example, a rabbit anti-mouse IgG antibody is used as the antibody. The fixation method is carried out by causing 11-Mercaptoundecanoic acid ethanol solution, 1-Ethyl-3-[3-dimethylaminopropyl]carbodiimide hydrochloride solution, N-Hydroxysulfosuccinimide solution, and rabbit anti-mouse IgG antibody/tris-hydrochloric acid buffers as in the example 1 to flow sequentially inside the flow channel.

Subjected to the above described operations, the detection element with a rabbit anti-mouse IgG antibody as a capturing body can be produced inside the flow channel.

Next, an example of detection apparatus provided with the detection element will be described. Here, the present example is an example of carrying out detection with light transmitted through the detection element.

FIGS. 11A and 11B are diagrams schematically illustrating the detection apparatus according to the present example, FIG. 11A being a perspective view and FIG. 11B being a sectional view. The detection apparatus includes a detection element including metal-containing members 119 and the like arranged inside the channel flow 114, a light source 115 and a light receiving element 116. Accordingly, the position of the light source at the time of detection is a position capable of irradiation measurement light 117 including parallel components to the long axis direction of the metal-containing members 119 inside the detection element as schematically illustrated in FIGS. 11A and 11B. The position of the light receiving element 116 is a position capable of detecting property of the measurement light 118 transmitted through the detection element. Here, otherwise, a spectordetector not illustrated in the drawing may be provided in the light receiving element. Moreover, an arithmetic apparatus computing the detected property change and a display unit displaying the detection results, a unit, such as a pump, sending samples to inside the flow channel and the like are not illustrated in the drawing but preferably provided.

Next, an example of a detection method with the above described detection apparatus will be described.

At first, the detection element, the light source and the light receiving element are arranged to establish the above described positional relation and a spectrum is detected. Thereafter a sample made of phosphoric acid buffers including mouse IgG likewise in the example 5 is introduced into inside the flow channel 114; sent; and brought into contact with the detection element and reaction with a capturing body. After that reaction, the phosphoric acid buffers are preferably introduced and sent to inside the flow channel to carry out cleaning. Thereafter again, the detection element, the light source and the light receiving element are arranged to establish a likewise positional relation likewise at the time of the above described detection and a spectrum is detected.

Here, target substance concentration can be obtained by obtaining calibration curve as in the example 5.

In addition, likewise in the example 5, the spectrum change can be change in spectrum peak wavelength and change in peak shape of the spectrum peak can be used. Moreover, optical intensity at one or a plurality of wavelength points may be used. In addition, the present invention is configured by the detection element being provided in the flow channel. Therefore, sending solution and continuing detection, chronological change and change in reacted amount can be detected.

Example 10

The present example is an example of producing tubular metal-containing members with surfaces of glycolipid hollow tubes covered by gold film and, moreover, fixating a rabbit anti-mouse IgG antibody on the surfaces of those tubular metal-containing members as a capturing body.

At first, tubular metal-containing members with surfaces of glycolipid hollow tubes covered by gold film are produced.

<Synthesis of Sugar Amide Lipid Tube>

At first sodium acid carbonate in the amount of 10 g is added to D-(+)-glucose solution (containing glucose in the amount of 1 g) in the amount of 25 ml and sodium acid carbonate is gradually added so as to reach a sum of 50 g and the mixture is agitated at 37° C. for 5 days.

After confirming reaction with thin layer chromatography (developing solvent: acetic ether/acetic acid/methanol/water=4/3/3/1 (reduction in quantitative ratio)), the reactive solution is cooled to 5° C. and sodium acid carbonate is deposited. Thereafter the supernatant undergoes desalination with a micro-acilyzer G1 (both being produced by ASTOM Corporation) with an ion exchange AC-110-10 cartridge mounted thereon and is frozen and dried to obtain D-glucopyranosylamine.

Next, dimethylsulfoxide (hereunder occasionally to be described as DMSO) in the amount of 1 ml including 13-cis-octadecene acid in the amount of 350 mg is added to DMSO in the amount of 0.5 ml including 1-hydroxybenzotriazole in the amount of 190 mg and (benzotriazol-1-yloxy)-tris-(dimethylamino) phosphonium hexafluorophosphate in the amount of 1.65 g and the mixture is agitated for 10 minutes and brought into reaction. Thereafter, DMF in the amount of 1.5 ml with the foregoing synthesized D-glucopyranosylamine in the amount of 877 mg being dissolved is added and the mixture is agitated at 37° C. for 45 hours. The target is separated with a silica gel column (TSKgel-40S; produced by Tosoh Corporation; developing solvent: chloroform/methanol=5/1) and collected. With TEM observation, the measurements of the sugar amide lipid tube is confirmed with outer diameter being around 200 nm and inner diameter being around 70 nm (operations described above follow Langmuir 2005, 21, p.p. 743-750).

<Synthesis of Gold Fine Particles>

1M NaOH solution in the amount of 0.5 ml is added to deionized water in the amount of 45 ml and, moreover, THPC (Tetrakis (hydroxymethyl) phosphonium chloride) solution in the amount of 1 ml (produced by adding deionized water in the amount of 1 ml to 80% THPC solution in the amount of 12 μl (0.067 mmol)) and the mixture is violently agitated for 5 minutes. Thereafter, 1% HAuCl4 solution in the amount of 2 ml is added and is reacted. Thereby solution including gold fine particles with diameter of around 2 to 3 nm is obtained.

<Gold Coating to Sugar Amide Lipid Tube>

Gold fine particle dispersion liquid in the amount of 5 ml is added to the sugar amide lipid tube solution in the amount 0.5 ml and the mixture is agitated for several minutes and thereafter left still for 2 hours. Thereafter, centrifugation is carried out to remove the supernatant. The deionized water is newly added to carry out resuspension to obtain a sugar amide lipid tube with gold fine particles being fixated on the outer surfaces.

Aside from that operation, potassium carbonate in the amount of 25 mg is added to the deionized water in the amount of 100 ml and the mixture is agitated for 10 minutes. Thereafter 1% HAuCl4 solution in the amount of 1.5 ml is added. The mixture is left still until the reactive liquid originally colored yellow becomes colorless.

Formerly prepared gold fine particle fixating the sugar amide lipid tube liquid is added to the obtained colorless solution and, moreover, formaldehyde is added thereto and the mixture is reacted. The mixing ratio of the colorless solution and the gold fine particle fixating sugar amide lipid tube dispersion liquid can be appropriately determined according to thickness and mode of the desired gold coating layer. Here, formaldehyde is an example of reducing agent. An additive amount is determined appropriately according to the above described mixing ratio. In addition, reduction treatment can be selected from the group consisting of addition of a reducing agent, pH adjustment, heating, light irradiation, ultrasonic processing and the like.

With the method as described above, the gold coating sugar amide lipid tube is obtained.

A rabbit anti-mouse IgG antibody is fixated onto the obtained gold coating sugar amide lipid tube with the method likewise in the example 1 and, thereby, detection material made of gold coating sugar amide lipid tube and including a rabbit anti-mouse IgG antibody as a capturing body can be produced.

The present material likewise the material obtained in the example 1 can be served for the methods in the examples 2 to 9.

As described above, according to exemplary embodiments of the present invention, a plurality of tubular metal-containing members are arranged on a substrate with a given orientation; thereby, plasmon resonance can be utilized efficiently; and wavelength shift amount of the plasmon resonance peak increases. Thereby, sensitivity at an occasion of target substance detection utilizing plasmon resonance is improved.

This application claims the benefit of Japanese Patent Application No. 2006-315715, filed Nov. 22, 2006, which is hereby incorporated by reference herein in its entirety.

What is claimed is:

1. A detection apparatus detecting a target substance in a sample by utilizing plasmon resonance, comprising:
   a detection element obtaining information on the target substance in the sample by being contacted with the sample;
   a light source for irradiating light to the detection element; and
   a light receiving element for receiving the light emitted from the light source and reflected from or transmitted through the detection element,
   wherein the detection element comprises a substrate and a plurality of metal-containing members arranged on the substrate,
   wherein the metal-containing members are tubular in shape and the metal-containing members are arranged on the substrate with a given orientation, and
   wherein each of the metal-containing members includes, on a surface thereof, a capturing body capturing the target substance in the sample.

2. A method of detecting target substance in a sample by utilizing plasmon resonance, comprising:
   contacting a detection element with a sample;
   irradiating light to the detection element; and receiving light reflected from or transmitted through the detection element,
   wherein the detection element comprises a substrate and a plurality of metal-containing members arranged on the substrate,
   wherein the metal-containing members are tubular in shape and the metal-containing members are arranged on the substrate with a given orientation, and
   wherein each of the metal-containing members includes, on a surface thereof, a capturing body capturing the target substance in the sample.

3. The method of detecting target substance according to claim 2, wherein the light-irradiating step is a step of irradiating a polarized light.

4. The method of detecting target substance according to claim 3, wherein the polarized light is biased with an direction of oscillation of an electric filed component being parallel to long axis directions of the tubular metal-containing members.

* * * * *